US007943683B2

(12) United States Patent
Rizk et al.

(10) Patent No.: US 7,943,683 B2
(45) Date of Patent: May 17, 2011

(54) MEDICAL DEVICES CONTAINING ORIENTED FILMS OF POLY-4-HYDROXYBUTYRATE AND COPOLYMERS

(75) Inventors: Said Rizk, Salem, NH (US); David P. Martin, Arlington, MA (US); Kicherl Ho, Newton, MA (US); Simon F. Williams, Sherborn, MA (US)

(73) Assignee: Tepha, Inc., Lexington, MA (US)

(*) Notice: Subject to any disclaimer, the term of this patent is extended or adjusted under 35 U.S.C. 154(b) by 631 days.

(21) Appl. No.: 11/931,850

(22) Filed: Oct. 31, 2007

(65) Prior Publication Data
US 2008/0132602 A1 Jun. 5, 2008

Related U.S. Application Data

(60) Provisional application No. 60/868,182, filed on Dec. 1, 2006.

(51) Int. Cl.
C08G 63/06 (2006.01)
B29C 47/00 (2006.01)

(52) U.S. Cl. ... 523/113; 523/115; 528/354; 264/177.17; 264/211.12

(58) Field of Classification Search .................. 523/115, 523/113; 528/354; 264/177.17, 211.12
See application file for complete search history.

(56) References Cited

U.S. PATENT DOCUMENTS

| | | | |
|---|---|---|---|
| 3,598,122 A | 8/1971 | Zaffaroni et al. |
| 3,598,123 A | 8/1971 | Zaffaroni et al. |
| 3,731,683 A | 5/1973 | Zaffaroni |
| 3,797,494 A | 3/1974 | Zaffaroni |
| 3,982,543 A | 9/1976 | Schmitt et al. |
| 4,031,894 A | 6/1977 | Urquhart et al. |
| 4,201,211 A | 5/1980 | Chandrasekaran et al. |
| 4,205,399 A | 6/1980 | Jamiolkowski |
| 4,286,592 A | 9/1981 | Chandrasekaran |
| 4,314,557 A | 2/1982 | Chandrasekaran |
| 4,379,454 A | 4/1983 | Campbell et al. |
| 4,435,180 A | 3/1984 | Leeper |
| 4,537,738 A | 8/1985 | Holmes |
| 4,559,222 A | 12/1985 | Enscore et al. |
| 4,573,995 A | 3/1986 | Chen et al. |
| 4,588,580 A | 5/1986 | Gale et al. |
| 4,603,070 A | 7/1986 | Steel et al. |
| 4,645,502 A | 2/1987 | Gale et al. |
| 4,648,978 A | 3/1987 | Makinen et al. |
| 4,664,655 A | 5/1987 | Orentreich et al. |
| 4,704,282 A | 11/1987 | Campbell et al. |
| 4,711,241 A | 12/1987 | Lehmann |
| 4,758,234 A | 7/1988 | Orentreich et al. |
| 4,788,062 A | 11/1988 | Gale et al. |
| 4,792,336 A | 12/1988 | Hlavacek et al. |
| 4,816,258 A | 3/1989 | Nedberge et al. |
| 4,826,493 A | 5/1989 | Martini |
| 4,849,226 A | 7/1989 | Gale |
| 4,853,226 A | 8/1989 | Machida et al. |
| 4,856,188 A | 8/1989 | Sibalis |
| 4,876,331 A | 10/1989 | Doi |
| 4,880,592 A | 11/1989 | Martini et al. |
| 4,908,027 A | 3/1990 | Enscore et al. |
| 4,910,145 A | 3/1990 | Holmes et al. |
| 4,938,763 A | 7/1990 | Dunn et al. |
| 4,943,435 A | 7/1990 | Baker et al. |
| 5,002,067 A | 3/1991 | Berthelsen et al. |
| 5,026,381 A | 6/1991 | Li |
| 5,032,638 A | 7/1991 | Wang et al. |
| 5,041,100 A | 8/1991 | Rowland et al. |
| 5,085,629 A | 2/1992 | Goldberg et al. |
| 5,124,371 A | 6/1992 | Tokiwa et al. |
| 5,128,144 A | 7/1992 | Korsatko-Wabnegg |
| 5,171,308 A | 12/1992 | Gallagher et al. |
| 5,204,382 A | 4/1993 | Wallace et al. |
| 5,236,431 A | 8/1993 | Gogolewski et al. |
| 5,245,023 A | 9/1993 | Peoples et al. |
| 5,250,430 A | 10/1993 | Peoples et al. |
| 5,271,961 A | 12/1993 | Mathiowitz et al. |

(Continued)

FOREIGN PATENT DOCUMENTS
CA 2307637 5/1999
(Continued)

OTHER PUBLICATIONS

Kaufman et al., An Overview of gamma-Hydroxybutylate Catabolism: The Role of the Cytosolic NADP (+)-Dependent Oxidoreductase EC 1.1.1.19 and of a Mitochondrial Hydroxyacid-Oxoacid Transhydrogenase in the Initial, Rate-Limiting Step in This Pathway, Neurochemical Research, vol. 16, No. 9, 1991, pp. 965-974.*
Williams & Peoples, "Making plastics green", *Chem. Br.*, 33:29-32 (1997).
Williams, et al., "PHA applications: addressing the price performance issue. I. Tissue engineering", *Int. J. Biol. Macromol.*, 25(1-3):111-121 (1999).
Wodzinska, et al., "Polyhydroxybutyrate synthase: Evidence for covalent catalysis", *J. Am. Chem. Soc.*, 118:6319-6320 (1996).

(Continued)

Primary Examiner — Tae H Yoon
(74) Attorney, Agent, or Firm — Pabst Patent Group LLP

(57) ABSTRACT

Continuous processing methods for making absorbable polymeric films with one or more of the following properties: high toughness, low modulus, high tensile strength, and thickness less than 10 mm, more preferably less than 1 mm, and more preferably less than 100 μm, have been developed. In the preferred embodiment, the polymer is a polyhydroxyalkanoate, and in the most preferred embodiment, the polymer comprises 4-hydroxybutyrate. A particularly preferred embodiment is a film of poly-4-hydroxybutyrate or copolymer thereof, wherein the film has a tensile strength greater than 5.5 kgf/mm$^2$, tensile modulus less than 181 kgf/mm$^2$, and elongation at break from 10-500%, wherein the film is derived by a continuous process such as melt extrusion or solvent casting, followed by orientation to more than 25% of the film's original length in one or more directions. These can be used for a variety of purposes including fabrication of medical devices.

16 Claims, No Drawings

U.S. PATENT DOCUMENTS

| | | | |
|---|---|---|---|
| 5,278,201 A | 1/1994 | Dunn et al. | |
| 5,278,202 A | 1/1994 | Dunn et al. | |
| 5,278,256 A | 1/1994 | Bellis | |
| 5,292,860 A | 3/1994 | Shiotani et al. | |
| 5,306,286 A | 4/1994 | Stack et al. | |
| 5,334,698 A | 8/1994 | Witholt et al. | |
| 5,386,004 A * | 1/1995 | Obuchi et al. | 528/354 |
| 5,443,458 A | 8/1995 | Eury | |
| 5,468,253 A | 11/1995 | Bezwada et al. | |
| 5,480,394 A | 1/1996 | Ishikawa | |
| 5,480,794 A | 1/1996 | Peoples et al. | |
| 5,489,470 A | 2/1996 | Noda | |
| 5,502,116 A | 3/1996 | Noda | |
| 5,502,158 A | 3/1996 | Sinclair et al. | |
| 5,512,669 A | 4/1996 | Peoples et al. | |
| 5,516,565 A | 5/1996 | Matsumoto | |
| 5,516,883 A | 5/1996 | Hori et al. | |
| 5,534,432 A | 7/1996 | Peoples et al. | |
| 5,536,564 A | 7/1996 | Noda | |
| 5,550,173 A | 8/1996 | Hammond et al. | |
| 5,551,954 A | 9/1996 | Buscemi et al. | |
| 5,563,239 A | 10/1996 | Hubbs et al. | |
| 5,584,885 A | 12/1996 | Seckel | |
| 5,614,576 A | 3/1997 | Rutherford et al. | |
| 5,625,030 A | 4/1997 | Williams et al. | |
| 5,629,077 A | 5/1997 | Turnlund et al. | |
| 5,635,215 A | 6/1997 | Boschetti et al. | |
| 5,646,217 A | 7/1997 | Hammond | |
| 5,648,100 A | 7/1997 | Boschetti et al. | |
| 5,670,161 A | 9/1997 | Healy et al. | |
| 5,703,160 A | 12/1997 | Dehennau et al. | |
| 5,705,187 A | 1/1998 | Unger | |
| 5,709,854 A | 1/1998 | Griffith-Cima et al. | |
| 5,711,933 A | 1/1998 | Bichon et al. | |
| 5,728,752 A | 3/1998 | Scopelianos et al. | |
| 5,735,863 A | 4/1998 | Della Valle et al. | |
| 5,753,364 A | 5/1998 | Rutherford et al. | |
| 5,753,708 A | 5/1998 | Koehler et al. | |
| 5,789,536 A | 8/1998 | Liggat et al. | |
| 5,811,272 A | 9/1998 | Snell | |
| 5,814,071 A | 9/1998 | McDevitt et al. | |
| 5,814,599 A | 9/1998 | Mitragotri et al. | |
| 5,824,333 A | 10/1998 | Scopelianos et al. | |
| 5,824,751 A | 10/1998 | Hori et al. | |
| 5,834,582 A | 11/1998 | Sinclair et al. | |
| 5,840,331 A | 11/1998 | Van Cauter et al. | |
| 5,842,477 A | 12/1998 | Naughton et al. | |
| 5,855,619 A | 1/1999 | Caplan et al. | |
| 5,874,040 A | 2/1999 | Liggat et al. | |
| 5,876,452 A | 3/1999 | Athanasiou et al. | |
| 5,876,455 A | 3/1999 | Harwin | |
| 5,879,322 A | 3/1999 | Lattin et al. | |
| 5,917,002 A * | 6/1999 | Doi et al. | 528/328 |
| 5,919,478 A | 7/1999 | Landrau et al. | |
| 5,935,506 A | 8/1999 | Schmitz et al. | |
| 5,990,162 A | 11/1999 | Scharf | |
| 5,994,478 A | 11/1999 | Asrar et al. | |
| 6,056,970 A | 5/2000 | Greenawalt et al. | |
| 6,119,567 A | 9/2000 | Schindler et al. | |
| 6,214,387 B1 | 4/2001 | Berde et al. | |
| 6,245,537 B1 | 6/2001 | Williams | |
| 6,316,262 B1 | 11/2001 | Huisman | |
| 6,323,010 B1 | 11/2001 | Skraly | |
| 6,454,811 B1 | 9/2002 | Sherwood et al. | |
| 6,514,515 B1 | 2/2003 | Williams | |
| 6,548,569 B1 | 4/2003 | Williams | |
| 6,555,123 B2 | 4/2003 | Williams | |
| 6,585,994 B2 | 7/2003 | Williams | |
| 6,600,010 B2 | 7/2003 | Mao et al. | |
| 6,610,764 B1 | 8/2003 | Martin | |
| 6,623,748 B2 | 9/2003 | Clokie | |
| 6,656,489 B1 | 12/2003 | Mahmood et al. | |
| 6,680,046 B1 | 1/2004 | Boschetti | |
| 6,770,356 B2 | 8/2004 | O'Donnell et al. | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,248 B2 | 4/2005 | Signer et al. | |
| 6,878,758 B2 | 4/2005 | Williams | |
| 6,905,987 B2 | 6/2005 | Noda | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,553,923 B2 | 6/2009 | Williams et al. | |
| 2002/0028243 A1 | 3/2002 | Masters | |
| 2002/0156150 A1 | 10/2002 | Williams et al. | |
| 2002/0173558 A1 | 11/2002 | Williams et al. | |
| 2003/0091803 A1 | 5/2003 | Bond et al. | |
| 2003/1018589 | 10/2003 | Buiser et al. | |
| 2003/0211131 A1 | 11/2003 | Martin | |
| 2004/0220355 A1 * | 11/2004 | Whitehouse | 525/436 |
| 2004/0234576 A1 | 11/2004 | Martin et al. | |
| 2005/0025809 A1 | 2/2005 | Hasirci et al. | |
| 2005/0107505 A1 | 5/2005 | Shinoda et al. | |
| 2005/0137678 A1 | 6/2005 | Varma | |
| 2005/0267516 A1 | 12/2005 | Soleimani | |
| 2006/0058470 A1 | 3/2006 | Rizk | |
| 2006/0177513 A1 | 8/2006 | Martin et al. | |
| 2006/0287659 A1 | 12/2006 | Terenghi et al. | |
| 2007/0010851 A1 * | 1/2007 | Chanduszko et al. | 606/213 |
| 2008/0051490 A1 | 2/2008 | Williams et al. | |

FOREIGN PATENT DOCUMENTS

| | | |
|---|---|---|
| CA | 2259098 | 7/1999 |
| CA | 2298421 | 2/2000 |
| DE | 39 37 649 | 5/1991 |
| EP | 0 258 781 | 3/1988 |
| EP | 0 344 704 | 12/1989 |
| EP | 0 349 505 | 3/1990 |
| EP | 0 423 484 | 4/1991 |
| EP | 0 429 403 | 5/1991 |
| EP | 0 432 443 | 6/1991 |
| EP | 0 452 111 | 10/1991 |
| EP | 0 507 554 | 10/1992 |
| EP | 0 601 885 | 6/1994 |
| EP | 0 628 586 | 12/1994 |
| EP | 0 754 467 | 1/1997 |
| EP | 1130043 | 9/2001 |
| EP | 1266984 | 12/2002 |
| GB | 2166354 | 5/1986 |
| JP | 62-209144 | 9/1987 |
| JP | 03-187386 | 8/1991 |
| JP | 04-292619 | 10/1992 |
| JP | 04-326932 | 11/1992 |
| JP | 5-023189 | 2/1993 |
| JP | 5-194141 | 11/1993 |
| JP | 06-264306 | 9/1994 |
| JP | 06-336523 | 12/1994 |
| JP | 07-275344 | 10/1995 |
| JP | 08-089264 | 4/1996 |
| JP | 09-098793 | 4/1997 |
| JP | 09-507091 | 7/1997 |
| WO | WO 92/18164 | 10/1992 |
| WO | WO 93/05824 | 4/1993 |
| WO | WO 93/20134 | 10/1993 |
| WO | WO 94/02184 | 2/1994 |
| WO | WO 94/06886 | 3/1994 |
| WO | WO 95/03356 A1 | 2/1995 |
| WO | WO 95/17216 | 6/1995 |
| WO | WO 95/20614 | 8/1995 |
| WO | WO 95/20615 | 8/1995 |
| WO | WO 95/20621 | 8/1995 |
| WO | WO 95/23250 | 8/1995 |
| WO | WO 95/33874 A1 | 12/1995 |
| WO | WO 96/00263 A1 | 1/1996 |
| WO | WO 96/08535 A1 | 3/1996 |
| WO | WO 96/18420 A1 | 6/1996 |
| WO | WO 96/21427 | 7/1996 |
| WO | WO 96/40304 | 12/1996 |
| WO | WO 97/04036 | 2/1997 |
| WO | WO 97/07153 A1 | 2/1997 |
| WO | WO 97/15681 | 5/1997 |
| WO | WO 97/30042 | 8/1997 |
| WO | WO 98/04292 | 2/1998 |
| WO | WO 98/39453 | 9/1998 |

| WO | WO 98/48028 | 10/1998 |
| WO | WO 98/51812 | 11/1998 |
| WO | WO 99/11196 | 3/1999 |
| WO | WO 99/14313 | 3/1999 |
| WO | WO 99/32536 | 7/1999 |
| WO | WO 99/35192 | 7/1999 |
| WO | WO 00/51662 | 9/2000 |
| WO | WO 00/56376 | 9/2000 |
| WO | WO 01/10421 | 2/2001 |
| WO | WO 01/15671 | 3/2001 |
| WO | WO 01/19361 | 3/2001 |
| WO | WO 2004/101002 | 11/2004 |

OTHER PUBLICATIONS

Wong & Mooney, "Synthesis and properties of bioabsorbable polymers used as synthetic matrices for tissue engineering", *Synthetic Bioabsorbable Polymer Scaffolds* (Atala, et al., eds.), pp. 51-82, Birkhäuser: Boston, 1997.

Worsey & Williams, "Metabolism of toluene and xylenes by *Pseudomonas putida* (arvilla) mt-2: evidence for a new function of the TOL plasmid", *J Bacteriol*, 124:7.13 (1975).

Xie, et al., "Ring-opening Polymerization of β-Butyrolactone by Thermophilic Lipases", *Macromolecules*, 30:6997-6998 (1997).

Yagmurlu, et al., "Sublactam cefoperazone polyhydroxybutyrate-co-hydroxyvalerate Local antibiotic delivery system: In Vivo Effectivness and Biocompatibility in the treatment of Implant-Related Experimental Osteomyelitis", *J. Biomed. Mater. Res.*, 46(4):494-503 (1999).

Yamada, et al., "Development of a dural substitute from synthetic bioabsorbable polymers", *J. Neurosurg.*, 86(6):1012-1017 (1997).

Yiu, et al., "Glial inhibition of CNS axon regeneration", *Nat. Rev. Neurosci.*, 7:617-627(2006).

Zund, et al., "The in vitro construction of a tissue engineered bioprosthetic heart valve", *Eur. J. Cardiothorac. Surg.*, 11(3):493-497 (1997).

U.S. Appl. No. 12/270,911, filed Sep. 10, 2008, Terenchi, et al.

Abate, et al., "Separation and structural characterizations of cyclic and open chain oligomers produced in the partial pyrolysis of microbial poly(hydroxyutyrates)", *Macromolecules*, 28(23):7911-1916 (1995).

Addolorato, et al., "Maintaining abstinence from alcohol with gamma-hydroxybutyric acid", *The Lancet*, 351:38 (1998).

Agostini, et al., "Synthesis and Characterization of Poly-β-Hydroxybutyrate. I. Synthesis of Crystalline DL Poly-β-Hydroxybutyrate from DL-β-Butyrolactone", *Polym. Sci. Part A-1*, 9:2775-2787 (1971).

Akhtar, "Physiomechanical Properties of bacterial P(HB-HV) Polyesters and Their Uses in drug Delivery", The British Library Document Supply Centre , UMI (1990).

Anderson, et al., "Occurrence, metabolism, metabolic role and industrial uses of bacterial polyhydroxyalkanoates", *Microbiol. Rev.*, 54:450-472 (1990).

Andriamampandry, et al., "Cloning of a rat brain succinic semialdehyde reductase involved in the synthesis of the neuromodulator g—hydroxybutyrate", *Biochem. J.*, 334:43-50 (1998).

Bailey, "Free radical ring-opening polymerization", *J. Polym. Preprints*, 25:210-211 (1984).

Bailey, et al., "Synthesis of Poly-∈-caprolactone via a free radical mechanism. Free radical ring-opening polymerization of 2-methylene-1,3-dioxepane", *J. Polym. Sci. Polym. Chem.*, 20:3021-3030 (1982).

Bandiera, et al., "Effect of sodium sulfonate groups on the ionic conductivity of a copolyester of thiodipropionic acid", *Eur. Pol. J.*, 33:1679-1683 (1997).

Behrend, "PHB as a bioresorbable material for intravascular stents", *American J. Cardiol.*, TCT Abstracts, p. 45 (1998).

Berde, et al., "Sustained release of dibucaine from a biodegradable polymer matrix: A potential method for prolonged neural blockade", *Abstracts of Scientific Papers, 1990 Annual Meeting, Amer. Soc. Anesthesiologists*, 73(3A):A776 (1990).

Berger, et al., "PHB recovery by hypochlorite digestion of non-PHB biomass", *Biotechnonology Techniques*, 3(4):227-232 (1989).

Blight, "Miracles and molecules—progress in spinal cord repair.", *Nat Neurosci.*, 5:1051-1054 (2002).

Boeree, et al., "Development of a degradable composite for orthopaedic use: mechanical evaluation of an hydroxyapatite-polyhydroxybutyrate composite material", *Biomaterials*, 14(10):793-796 (1993).

Brandl, et al., "*Pseudomonas oleovorans* as a source of poly(b-hydroxyalkanoates for potential applications as biodegradable polyesters", *Appl. Environ. Microbiol.*, 54:1977-1982 (1988).

Braunegg, et al., "Polyhydroxyalkanoates, biopolyesters from renewable resources: physiological and engineering aspects", *J. Biotechnology*, 65:127-161 (1998).

Breuer, et al., "Tissue Engineering Lamb Heart Valve Leaflets", *Biotechnology & Bioengineering*, 50:562-567 (1996).

Bruhn & Müller, "Preparation and characterization of spray-dried Poly(DL-Lactide) Micro Spheres", *Proceed. Intern. Symp. Control. Rel. Bioact. Mater.*, 18:668-669 (1991).

Byrom, "Miscellaneous Biomaterials", *Biomaterials* (Byrom, ed.), pp. 333-359, MacMillan Publishers: London, 1991.

Campbell & Bailey, "Mechanical properties of suture materials in vitro and after in vivo implantation in horses", *Vet. Surg.*, 21(5):355-361 (1992).

Clavijo-Alvarez, et al. "Comparison of biodegradable conduits within aged rat sciatic nerve defects", *Plast Reconstr Surg.*, 119(6):1839-1851(2007).

Colombo, at al., "Involvement of GABA(A) and GABA(B) receptors in the mediation of discriminative stimulus effects of gamma-hydroxybutyric acid", *Physiology & Behavior*, 64:293-302 (1998).

Conti, et al., "Use of polylactic acid for the preparation of microparticulate drug delivery systems", *J. Microencapsulation*, 9:153-166 (1992).

Cookson, "It grows on trees", *Financial Times*, p. 6 (Aug. 12, 1992).

Cuebas, et al., "Mitochondrial metabolism of 3-mercaptopropionic acid. Chemical synthesis of 3-mercaptopropionyl coenzyme A and some of its S-acyl derivatives", *J. Biol. Chem.*, 260:7330-7336 (1985).

Damien & Parsons, "Bone graft and bone graft substitutes: a review of current technology and applications", *J. Appl. Biomater.*, 2(3):187-208 (1991).

Dayton, et al., "Use of an absorbable mesh to repair contaminated abdominal-wall defects", *Archives of Surgery*, 121(8):954-960 (1986).

De Groot, "Meniscal tissue regeneration in porous 50/50 copoly(L-lactide/epsilon-caprolactone) implants", *Biomaterials*, 18(8):613-622 (1997).

De Koning, et al., "A biodegradable rubber by crosslinking poly(hydroxyalkanoate) from *Pseudomonas oleovorans*", *Polymer*, 35:2090-2097 (1994).

De Smet, et al., "Characterization of Intracellular Inclusions Formed by *Pseudomonas olevorans* During Growth on Octane", J. Bacterial., 154(1):870-878 (1983).

Dubois, et al., "Macromolecular engineering of polylactones and polylactides. 12. Study of the depolymerization reactions of pol(e-caprolactone) with functional aluminum alkoxide end groups", *Macromolecules*, 26:4407-4412 (1993).

Duvernoy, et al. "A biodegradable patch used as a pericardial substitute after cardiac surgery: 6- and 24-month evaluation with CT", *Thorac. Cardiovasc. Surg.*, 43(5):271-274 (1995).

Entholzner, et al., "EEG changes during sedation with gamma-hydroxybutyric acid", *Anaesthesist*, 44:345-350 (1995).

Fraser, et al., "Controlled release of a GnRH agonist from a polyhydroxybutyric acid implant-reversible suppression of the menstrual cycle in the macaque", *Acta Endocrinol*, 121:841-848 (1989).

Freed, et al., "Biodegradable polymer scaffolds for tissue engineering", *Biotechnology*, 12:689-693 (1994).

Füchtenbusch, et al., "Biosynthesis of novel copolyesters containing 3-hydroxypivalic acid by Rhodoccus ruber NCIMB 40126 and related bacteria", *FEMS Microbiol. Lett.*, 159:85-92 (1998).

Fukuzaki, et al., "Direct copolymerization of L-lactic acid with ÿ-butyrolactone in the absence of catalysts", *Die Madromoleculare Chemie*, 190:1553-1559 (1989).

Gabbay, et al., "New outlook on pericardial substitution after open heart operations", *Ann. Thorac. Surg.*, 48(6):803-812 (1989).

Gagnon, et al., "A thermoplastic elastomer produced by the bacterium *Pseudomonas oleovarans*", *Rubber World*, 207:32-38 (1992).
Gagnon, et al., "Chemical modification of bacterial elastomers: 1. Peroxide crosslinking", *Polymer*, 35:4358-4367 (1994).
Gerngross & Martin, "Enzyme-catalyzed synthesis of poly[(R)-(−)-3-hydroxybutyrate]: formation of macroscopic granules in vitro", *Proc. Natl. Acad. Sci. USA*, 92:6279-6283 (1995).
Gerra, et al., "Flumazenil effects on growth hormone response to gamma-hydroxybutyric acid", *International Clinical Psychopharmacology*, 9:211-215 (1994).
Griebel, et al., "Metabolism of poly-beta-hydroxybutyrate. I. Purification, composition, and properties of native poly-beta-hydroxybutyrate granules from *Bacillus megaterium*", *Biochemistry*, 7:3676-3681 (1968).
Gross, et al., "Polymerization if b-monosubstituted-b-propiolactones using trialkylaminimum-water catalytic systems and polymer characterization", *Macromolecules*, 21:2657-2668 (1988).
Gugala, et al., "Regeneration of segmental diaphyseal defects in sheep tibiae using resorbable polymeric membranes: a preliminary study", *J. Orthop. Trauma.*, 13(3):187.195 (1999).
Gürsel, et al., "In vivo application of biodegradable controlled antibiotic release systems for the treatment of implant-related osteomyelitis", *Biomaterials*, 22:73-80 (2001).
Hadlock, et al., "Ocular cell monolayers cultured on biodegradable substrates", *Tissue Eng.*, 5(3):187-196 (1999).
Hazari, et al., "A new resorbable wrap-around implant as an alternative nerve repair technique", *J. Hand Surgery*, 24(3):291-295 (1999).
Hazari, et al., "A resorbable nerve conduit as an alternative to nerve autograft in nerve gap repair", *Br J Plast Surg.*, 52(8):653-657 (1999).
Hein, et al., "Biosynthesis of poly(4-hydroxybutyric acid) by recombinant strains of *Escherichia coli*", *FEMS Microbial. Lett.*, 153:411-418 (1997).
Heydorn, et al., "A new look at pericardial substitutes", *J. Thorac. Cardiovasc. Surg.*, 94:291-296 (1987).
Hocking & Marchessault, "Syndiotactic poly[(R,S)-β-hydroxybutyrate] isolated from methyaluminoxane-catalyzed polymerization", *Polym. Bull.*, 30:163-170 (1993).
Hocking & Marchessault, "Biopolyesters", *Chemistry and Technology of Biodegradable Polymers* (Griffin, ed.), pp. 48-96, Chapman and Hall: London, 1994.
Hoeke, "Mechanisms of Disease: what factors limit the success of peripheral nerve regeneration in humans?", *Nat. Clin. Pract. Neurol.*, 448-454 (2006).
Holmes, "Biologically Produced (R)-3-hydroxyalkanoate Polymers and Copolymers", *Developments in Crystalline Polymers* (Bassett, ed.), pp. 1-65, Elsevier: London, 1988.
Holmes, et al., "Applications of PHB—a microbially produced biodegradable thermoplastic", *Phys Technol*, 16:32-36 (1985).
Hori, et al., "Ring-Opening Copolymerization of Optically Active β-Butyrolactone with Several Lactones Catalyzed by Distannoxane Complexes: Synthesis of New Biodegradable Polyesters", *Macromolecules*, 26:4388-4390 (1993).
Hori, et al., "Ring-Opening Polymerization of Optically Active β-Butyrolactone Using Distannoxane Catalysts: Synthesis of High Molecular Wright Poly(3-hydroxybutyrate)", *Macromolecules*, 26:5533-5534 (1993).
Hori, et al., "Chemical synthesis of high molecular weight poly(3-hydroxybutyrate-co-4-hydroxybutyrate)", *Polymer*, 36(4): 4703-4705 (1995).
Horowitz, et al., "Novel Thermal Route to an Amorphous, Film-Forming Polymer Latex", *Macromolecules*, 32:3347-3352 (1999).
Horsch, "Inheritance of Functional Foreign Genes in Plants", *Science*, 223(4635):496-498 (1984).
Huijberts, et al., "*Pseudomonas putida* KT2442 cultivated on glucose accumulates poly(3-hydroxyalkanoates) consisting of saturated and unsaturated monomers", *Appl Environ Microbiol.*, 58(2):536-544 (1992).
Hutmacher, et al., "A review of material properties of biodegradable and bioresorbable polymers and devices for GTR and GBR applications", *Int. J. Oral Maxillofac. Implants*, 11(5):667-678 (1996).

Kameyama, et al., "Novel sequence-ordered polymers by transformation of polymer backbone: Quantitative and regioselective insertion of Thiranes into poly(S-aryl thioester)", *Macromol.*, 32:1407-1412 (1999).
Kassab, "Rifampicin carrying polyhydroxybutyrate microspheres as a potential chemoembolization agent", *Journal of Biomaterials Science, Polymer Edition*, 8(12):947-961 (1997).
Kassab, "Embolization with polyhydroxybutyrate (PHB) microspheres: In vivo studies", *J. Bioactive and Compatible Polymers*, 14:291-302 (1999).
Kaufman & Nelson, An overview of gamma-hydroxybutyrate catabolism: the role of the cytosolic NADP(+)-dependent oxidoreductase EC 1.1.1.19 and of a mitochondrial hydroxyacid-oxoacid transhydrogenase in the initial, rate-limiting step in this.
Keeler, "Plastics Grown in Bacteria Inch Toward the Market", *R&D Magazine*, 46-52 (1991).
Keeler, "Don't Let Food Go to Waste—Make Plastic Out of It", *R&D Magazine*, 52-57 (1991).
Kemnitzer, et al., "Preparation of predominantly Syndiotactic Poly(β-hydroxybutyrate) by the Tributylin Methoxide Catalyzed Ring-Opening Polymerization of racemic β-Butyrolactone", *Macromolecules*, 26:1221-1229 (1993).
Kim and Mooney, "Engineering smooth muscle tissue with a predefined structure", *J. Biomed. Mat. Res.*, 41(2):322-332 (1998).
Kishida, et al., "Formulation assisted biodegradeable polymer matrices", *Chemical and Pharmaceutical Bulletin, JP Pharm Society of Japan.*, 37(7)1954-1956(1989).
Kleinschmidt, et al., "Continuous sedation during spinal anaesthesia: gamma-hydroxybutyrate vs. propofol", *European Journal of Anaesthesiology*, 16:23-30 (1999).
Kleinschmidt, et al., "Total intravenous anaesthesia using propofol, gamma-hydroxybutyrate or midazolam in combination with sufentanil for patients undergoing coronary artery bypass surgery", *European Journal of Anesthesiology*, 14:590-599 (1997).
Klinge, et al., "Functional assessment and tissue response of short- and long-term absorbable surgical meshes", *Biomaterials*, 22:1415-1424 (2001).
Koosha, "Preparation and characterization of biodegradable polymeric drug carriers", Ph.D. Dissertation, 1989, Univ. Nottingham, UK., Diss. Abstr. Int. B 51:1206 (1990).
Koosha, et al., "Polyhydroxybutyrate as a drug carrier", *Crit. Rev. Ther. Drug Carrier Syst.*, 6(2):117-130 (1989).
Korkusuz, et al., "In vivo response to biodegradable controlled antibiotic release systems", *J. Biomed. Mater. Res.*, 55:217-228 (2001).
Korsatko, et al., "The influence of the molecular weight of poly-D(−)-3-hydroxybutyric acid on its use as a retard matrix for sustained drug release", *8th Europ. Congress of Biopharmaceutics and Pharmokinetics*, 1:234-242 (1987).
Korte & Gelt, "Hochdruckreaktionen. II. Die Polymerisation Von ÿ butyrolacton und ÿ-valerolactam bei hohen drücken", *Polymer Lett.*, 4:685-689 (1966).
Kusaka, et al., "Microbial synthesis and Physical Properties of ultra-high-molecular-weight poly[(R)-3-hydroxybutyrate]", *Pure Appl. Chem.*, A35:319-335 (1998).
Lafferty, et al., "Microbial Production of Poly-b-hydroxybutyric acid", *Biotechnology* (Rehm and Reed, Eds.), Verlagsgesellschaft: Weinheim, 66:135-176, 1988.
Le Borgne & Spassky, "Stereoelective polymerization of β-butyrolactone", *Polymer*, 30:2312-2319 (1989).
Lebedev and Yevstropv, "Thermoplastic properties of polylactones", *Makromol. Chem.*, 185:1235-1253 (1984).
Lee, et al., "Copolymerization of γ-butyrolactone and β-butyrolactone", *Macromol. Chem. Phys.*, 198:1109-1120 (1997).
Lemoigne & Roukhelman, "Fermentation b-Hydroxybutyrique", *Annales des Fermentations*, 5:527-536 (1925).
Ljungberg, et al. "Neuronal survival using a resorbable synthetic conduit as an alternative to primary nerve repair", *Microsurgery*, 19(6):259-264 (1999).
Lloyd, et al. "Transformation of *Arabidopsis thalania* with *Agrobacterium tumefaciens*", *Science*, 234:464-466 (1986).
Lütke-Eversloh, et al., "Identification of a new class of biopolymer: Bacterial synthesis of a sulfur-containing polymer with thioester linkages", *Microbiology*, 147(1):11-19 (2001).

Lütke-Eversloh, et al., "List of submitted abstracts", *The 8th International Symposium on Biological Polyesters*, (2000).

Madison & Huisman, "Metabolic engineering of poly(3-hydroxyalkanoates): from DNA to plastic", *Microbiology and Molecular Biology Reviews*, 63(1):21-53 (1999).

Malm, et al., "A new biodegradable patch for closure of atrial septal defect. An experimental study", *Scand. J. Thorac. Cardiovasc. Surg.*, 26(1):9-14 (1992).

Malm, et al., "Enlargement of the right ventricular outflow tract and the pulmonary artery with a new biodegradable patch in transannular position", *Eur. Surg. Res.*, 26(5):298-308 (1994).

Malm, et al., "Prevention of postoperative pericardial adhesions by closure of the pericardium with absorbable polymer patches. An experimental study", *J. Thorac. Cardiovasc. Surg.*, 104(3):600-607 (1992).

Mathiowitz & Langer, "Polyanhydride microspheres as drug delivery systems", *Microcapsules Nanopart. Med. Pharm.* (Donbrow, ed.), CRC Press: Boca Raton, pp. 99-123 (1992).

Maysinger, "Microencapsulation and the Grafting of Genetically Transformed Cells as Therapeutic Strategies to rescue Degenerating Neurons of the CNS", *Reviews in the Neurosciences*, 6:15-33 (1995).

McMillin, et al., "Elastomers for Biomedical Applications", *Rubber Chem. Technol.*, 67:417-446 (1994).

McWiliams, "Plastics as high as an elephant's eye?", *Business Week*, pp. 110-111 (Aug. 19, 1991).

Modelli, et al., "Kinetics of aerobic polymer degradation in soil by means of the ASTM D 5988-96 standard method", *J Environ Polym Degr*, 7:109-116 (1999).

Müh, et al., "PHA synthase from chromatium vinosum: cysteine 149 is involved in covalent catalysis", *Bioche.*, 38:826-837 (1999).

Müller & Seebach, "Poly(hydroxyalkanoates): A Fifth Class of Physiologically Important Organic Biopolymers", *Angew. Chem. Int. Ed. Engl.*, 32:477-502 (1993).

Nakamura, et al., "Biosynthesis and characteristics of bacterial poly(3-hydroxybutyrate-co-3-hydroxypropionate)", *Macromol. Rep.*, A28:15-24 (1991).

Nakamura, et al., "Microbial synthesis and characterization of poly(3-hydroxybutyrate-co-4-hydroxybutyrate)", *Macromol.*, 25:4237-4241 (1992).

Nelson, et al., "The extraneural distribution of gamma-hydroxybutyrate", *J. Neurochem.*, 37:1345-1348 (1981).

Niklason, et al., "Functional arteries grown in vitro", *Science*, 2845413):489-493 (1999).

Nobes, et al., "Polyhydroxyalkanoates: Materials for delivery systems", *Drug Del.*, 5:167-177(1998).

Ogawa, et al., "A New Technique to Efficiently Entrap Leuprolide Acetate into Microcapsules of Poly Lactic Acid or Copoly(Lactic/Glycolic) Acid", *Chem. Pharm. Bull.*, 36:1095-1103 (1988).

Otera, et al., "Distannoxane as reverse micelle-type catalyst: novel solvent effect on reaction rate of transesterification", *J. Org. Chem.*, 54:4013-4014 (1989).

Otera, et al., "Distannoxane-catalysed transesterification of 1, n-Dioldiacetates. Selective transformation of either of chemically equivalent functional groups", *J. Chem. Soc. Chem. Commun.*, 1742-1743 (1991).

Otera, et al., "Novel distannoxane-catalyzed transesterification and a new entry to a,b-unsaturated carboxylic acids", *Tetrahedron Lett.*, 27:2383-2386 (1986).

Otera, et al., "Novel template effects of distannoxanne catalysts in highly efficient transesterification and esterification", *J. Org. Chem.*, 56:5307-5311 (1991).

Pedrós-Alio, et al., "The influence of poly-b-hydroxybutyrate accumulation on cell volume and buoyant density in *Alcaligenes eutrophus*", *Arch. Microbiol.*, 143:178-184 (1985).

Peoples & Sinskey, "Poly-b-hydroxybutyrate in *Alcaligenes eutrophus* H16",*J. Biol. Chem.*, 264:15293-15297 (1989).

Peoples, et al., "Polyhydroxybutyrate (PHB): A Model System for Biopolymer Engineering: II", *Novel Biodegradable Microbial Polymers* (Dawes, ed.), pp. 191-202, Kluwer Academic Publishers: Netherlands (1990).

Perrin & English, "Polycaprolactone", *Handbook of Bioabsorbable Polymers* (Domb, et al., eds.), pp. 63-77, Harwood: Amsterdam, 1997.

Pinto, "Hydrogen Peroxide as depyrogenation agent for medical devices components", *Revista De Saude Publica*, 29(1):75-79 (1995).

Poirier, "Perspectives on the production of polyhydroxyalkanoates in plants", *FEMS Microbiology Reviews*, 103:237-246 (1992).

Poirier, et al., "Progress Toward Biologically Produced Biodegradable thermoplastics", *Adv. Mater.*, 5(1):30-37 (1993).

Pool, "In Search of the Plastic Potato", *Science*, 245:1187-1189 (1989).

Pouton & Akhtar, "Biosynthetic polyhydroxyalkanoates and their potential in drug delivery", *Advanced Drug Delivery Reviews*, 18:133-162 (1996).

Rehm & Steinbüchel, "Biochemical and genetic analysis of PHA synthases and other proteins required for PHA synthesis", *Int. J. Biol. Macromol.*, 25:3-19 (1999).

Renstad, et al., "The influence of processing induced differences in molecular structure on the biological and non-biological degradation of poly (3-hydroxybutyrate-co-3-hydroxyvalerate), P(3-HB-co-3-HV)", *Polymer Degradation and Stability*, 63:201-211 (1999).

Reynolds, *Martindale: The Extra Pharmacopeia, Thirty First Edition*, p. 1264, Royal Pharmaceutical Society: London, 1997.

Rivard, et al., "Fibroblast seeding and culture in biodegradable porous substrates", *J. Appl. Biomater.*, 6(1):65-68 (1995).

Ropero-Miller & Goldberger, "Recreational drugs. Current trends in the 90s", *Clinics in Laboratory Medicine*, 18:727.746 (1998).

Sabbagh, et al., "3-Mercaptopropionic acid, a potent inhibitor of fatty acid oxidation in rat heart mitochondria", *J. Biol. Chem.*, 260:7337-7342 (1985).

Saito & Doi, "Microbial synthesis and properties of poly(3-hydroxybutyrate-co-4-hydroxybutyrate) in *Comamonas acidovorans*", *Int. J. Biol. Macromol.*, 16:18 (1994).

Scharf, et al., "Pharmacokinetics of gammahydroxybutyrate (GHB) in narcoleptic patients", *Sleep*, 21:507-514 (1998).

Schlegel, et al., "Ein submersverfahren zur kultur wasserstofoxydierender bakterien: Wachstumsphysiologische untersuchungen", *Arch. Mikrobiol.*, 38:209-222 (1961).

Schlosshauer, "Synthetic nerve guide implants in humans: a comprehensive survey.", *Neurosurgery*, 59:740-748 (2006).

Schmidt, et al "Neural tissue engineering: strategies for repair and regeneration", *Annu. Rev. Biomed. Eng.*, 5:293-347 (2003).

Sendelbeck & Girdis, "Disposition of a 14C-labeled bioerodible polyorthoester and its hydrolysis products, 4-hydroxybutyrate and cis,trans-1,4-bis(hydroxymethyl)cyclohexane, in rats", *Drug Metabolism & Disposition*, 13:291-295 (1985).

Shinoka & Mayer, "New frontiers in tissue engineering: tissue engineered heart valves", *Synthetic Bioabsorbable Polymer Scaffolds* (Atala & Mooney, eds.), pp. 187-198, Birkhäuser: Boston, 1997.

Shinoka, et al., "Creation of viable pulmonary artery autografts through tissue engineering", *J. Thorac. Cardiovasc. Surg.*, 115(3):536-546 (1998).

Shinoka, et al., "Tissue engineering heart valves: valve leaflet replacement study in a lamb model", *Ann. Thorac. Surg.*, 60(6 Suppl):S513-516 (1995).

Sim, et al., "PHA synthase activity controls the molecular weight and polydispersity of polyhydroxybutyrate in vivo", *Nat. Blotechnol.*, 15(1):63-67 (1997).

Skrede, et al, "Thia fatty acids, metabolism and metabolic effects", *Biochim Biophys Acta*, 1344:115-131 (1997).

Snead, "The gamma-hydroxybutyrate model of absence seizures: correlation of regional brain levels of gamma-hydroxybutyric acid and gamma-butyrolactone with spike wave discharges", *Neuropharmacology*, 30:161-167 (1991).

Song, et al., "Production of poly(4-hydroxybutyric acid) by fed-batch cultures of recombinant strains of *Escherichia coli*", *Biotechnol. Lett.*, 21:193-197 (1999).

Speer & Warren, "Arthroscopic shoulder stabilization. A role for biodegradable materials", *Clin. Orthop.*, 291:67-74 (1993).

Stanton & Gagné, "The remarkable catalytic activity of alkali-metal alkoxide clusters in the ester interchange reaction", *J. Am. Chem. Soc.*, 119:5075.5076 (1997).

Steinbüchel & Wiese, "A *Pseudomonas* strain accumulating polyesters of 3-hydroxybutyric acid and medium-chain-length 3-hydroxyalkanoic acids", *Appl. Microbiol. Biotechnol.*, 37:691-697 (1992).

Steinbüchel, "Molecular basis for biosynthesis and accumulation of polyhydroxyalkanoic acids in bacteria", *FEMS Microbiol. Rev.*, 103:217-230 (1992).

Steinbüchel, "Polyhydroxyalkanoic Acids", *Biomaterials* (D. Byrom ed.), pp. 123-213, MacMillan Publishers: London, 1991.

Takagi et al., "Biosynthesis of polyhydroxyalkanoate with a thiophenoxy side group obtained from *Pseudomonas putida*", *Macromolecules*, 32: 8315-8318 (1999).

Talja, et al., "Bioabsorbable and biodegradable stents in urology", *J. Endourol.*, 11(6):391-397 (1997).

Tanahashi & Doi, "Thermal Properties and Stereoregularity of Poly(3-hydroxybutyrate) Prepared from optically Active β-Butyrolactone with a Zinc-Based Catalyst", *Macromolecules*, 24:5732-5733 (1991).

Tanaka, et al., "Clinical application of 4-hydroxybutyrate sodium and 4-butyrolactone in neuropsychiatric patients", *Folia Psychiatrica et Neurologica*, 20:9-17 (1966).

Tanguay, et al., "Current status of biodegradable stents", *Cardiol. Clin.*, 12(4):699-713 (1994).

Tepha announces submission of device master file to FDA (Jun. 3, 2002). Retrieved Dec. 17, 2004, from http://www.pressrelease.be/script_UK/newsdetail.asp?ndays=m&Id=695.

Tepha submits device master file to FDA—New Technology (Jul. 2, 2002). Retrieved on Dec. 17, 2004, from http://www.findarticles.com/p/articles/mi_mOPC/is_7_26/ai_89018276.

Tunnicliff, "Sites of action of gamma-hydroxybutyrate (GHB)—a neuroactive drug with abuse potential", *Clinical Toxicology*, 35:581-590 (1997).

Türesin, et al., "Biodegradable polyhydroxyalkanoate implants for osteomyelitis therapy: in vitro antibiotic release", *J. Biomater. Sci. Polymer Edn.*, 12:195-207 (2001).

Turke, "Absorbable Biomaterial is suited for diverse applications" (Jun. 2, 2002). Retrieved on Dec. 17, 2004, from http://www.devicelink.com/mpmn/archive/01/10/009.html.

Unverdorben, et al, "Polyhydroxybutyrate (PHB) Biodegradable Stent-Experience in the Rabbit", *American J. Cardiol.*, p. 46, TCT Abstracts (Oct. 1998).

Valappil, et al., "Biomedical applications of polyhydroxyalkanoates, an overview of animal testing and in vivo responses", *Expert Rev. Med. Devices*, 3(6):853-868 (2006).

Valentin, et al., "Identification of 5-hydroxyhexanoic acid, 4-hydroxyaheptanoic acid and 4-hydroxyoctanoic acid as new constituents of bacterial polyhydroxyalkanoic acids", *Appl. Microbiol. Biotechnol.*, 46:261-267 (1996).

Valentin & Dennis, "Production of poly(3-hydroxybutyrate-co-4-hydroxybutyrate) in recombinant *Escherichia coli* grown on glucose", *J. Biotechnol.*, 58:33-38 (1997).

Valentin, et al., "Identification of 4-hydroxyhexanoic acid as a constituent of biosynthetic polyhydroxyalkanoic acids from bacteria", *Appl. Microbiol. Biotechnol.*, 36:507-514 (1994).

Valentin, et al., "Identification of 4-hydroxyhexanoic acid as a new constituent of biosynthetic polyhydroxyalkanoic acids from bacteria", *Appl. Microbiol. Biotechnol.*, 40:710-716 (1994).

Von Schroeder, et al., "The use of polylactic acid matrix and periosteal grafts for the reconstruction of rabbit knee articular defects", *J. Biomed. Mater. Res.*, 25(3):329-339 (1991).

Wallen & Rohwedder, "Poly-b-hydroxyalkanoate from activated sludge", *Environ. Sci. Technol.*, 8:576-579 (1974).

Widmer & Mikos, "Fabrication of biodegradable polymer scaffolds for tissue engineering", *Frontiers in Tissue Engineering* (Patrick, et al., Eds.), pp. 107-120, Elsevier Science: New York, 1998.

Williams & Peoples, "Biodegradable plastics from plants", *Chemtech*, 26:38-44 (1996).

Williams & Peoples, "Making plastics green", *Chem. Br.*, 33:29-32 (1997).

Williams, et al., "PHA applications: addressing the price performance issue. I. Tissue engineering", *Int. J. Biol. Macromol.*, 25(1-3):111-121 (1999).

Wodzinska, et al., "Polyhydroxybutyrate synthase: Evidence for covalent catalysis", *J. Am. Chem. Soc.*, 118:6319-6320 (1996).

Wong & Mooney, "Synthesis and properties of bioabsorbable polymers used as synthetic matrices for tissue engineering", *Synthetic Bioabsorbable Polymer Scaffolds* (Atala, et al., eds.), pp. 51-82, Birkhäuser: Boston, 1997.

Xie, et al., "Ring-opening Polymerization of β-Butyrolactone by Thermophilic Lipases", *Macromolecules*, 30:6997-6998 (1997).

Yagmurlu, et al., "Sublactam cefoperazone polyhydroxybutyrate-co-hydroxyvalerate Local antibiotic delivery system: In Vivo Effectivness and Biocompatibility in the treatment of Implant-Related Experimental Osteomyelitis", *J. Biomed. Mater. Res.*, 46(4):494-503 (1999).

Yamada, et al., "Development of a dural substitute from synthetic bioabsorbable polymers", *J. Neurosurg.*, 86(6):1012-1017 (1997).

Yiu, et al., "Glial inhibition of CNS axon regeneration", *Nat. Rev. Neurosci.*, 7:617-627(2006).

Zund, et al., "The in vitro construction of a tissue engineered bioprosthetic heart valve", *Eur. J. Cardiothorac. Surg.*, 11(3):493-497 (1997).

\* cited by examiner

MEDICAL DEVICES CONTAINING ORIENTED FILMS OF POLY-4-HYDROXYBUTYRATE AND COPOLYMERS

RELATED APPLICATIONS

This application claims priority under 35 U.S.C. 119 to U.S. Ser. No. 60/868,182 filed Dec. 1, 2006, "Medical Devices Containing Oriented Films of Poly-4-Hydroxybutyrate and Copolymers" Said Rizk, David P. Martin, Kicherl Ho and Simon F. Williams.

FIELD OF THE INVENTION

The present invention generally relates to polymeric compositions that can be processed into films using continuous processes to produce products having substantially uniform physical properties, including physical and thermo-mechanical integrity. The compositions include polymers or copolymers comprising 4-hydroxybutyrate, and can be processed into films that are tough, have high strength and low modulus.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Cambridge, Mass.). Poly-4-hydroxybutyrate (P4HB, TephaFLEX® biomaterial) is a strong, pliable thermoplastic polyester that, despite its biosynthetic route, has a relatively simple structure

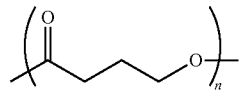

The polymer belongs to a larger class of materials called polyhydroxyalkanoates (PHAs) that are produced by numerous microorganisms (see, for example,: Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P4HB:

This schematic shows some of the known biosynthetic pathways for the production of P4HB. Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Chemical synthesis of P4HB has been attempted, but it has been impossible to produce the polymer with a sufficiently high molecular weight that is necessary for most applications (Hori, Y., et al., *Polymer* 36:4703-4705 (1995)).

U.S. Pat. Nos. 6,245,537, 6,623,748 and 7,244,442 describe methods of making PHAs with little to no endotoxin, which is suitable for medical applications. U.S. Pat. Nos. 6,548,569, 6,838,493, 6,867,247, 7,268,205, and 7,179,883 describe use of PHAs to make medical devices. Copolymers of P4HB include 4-hydroxybutyrate copolymerized with 3-hydroxybutyrate or glycolic acid (U.S. patent application No. 20030211131 by Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al.

Several patents including U.S. Pat. Nos. 6,555,123, 6,585,994, and 7,025,980 describe the use of PHAs in tissue repair and engineering.

In the practice of surgery there currently exists a need for absorbable films with improved performance. These films can be used, for example, to reinforce tissue structures. They may also be used as anti-adhesion membranes, or as components of other devices. A number of other absorbable materials have been used to produce films for use in surgery. For example, films have been made from polylactic acid (PLA) or copolymers containing the different stereoisomers of lactic acid or glycolic acid. SurgiWrap™, for example, is a medical film implant made from a copolymer of L-lactide and D,L-lactide, 70:30. These materials do not, however, have ideal properties for many procedures and applications. Films made

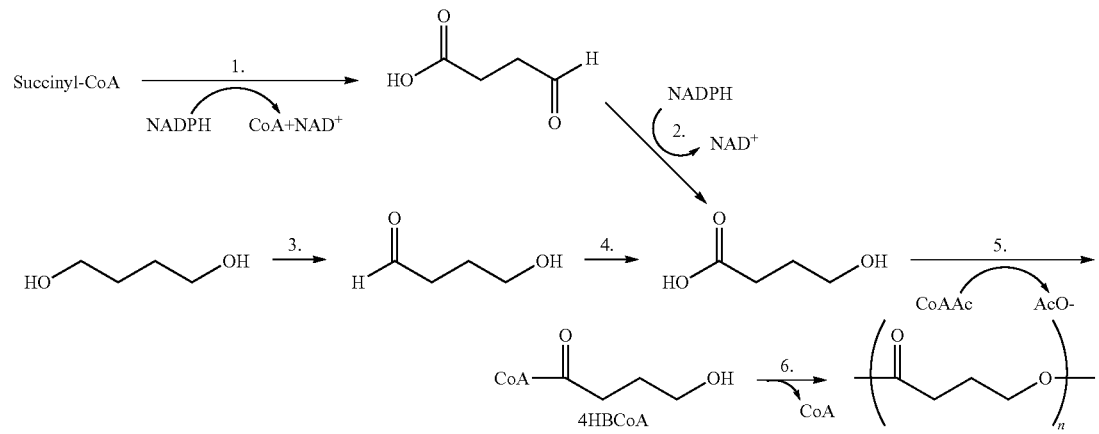

from PLA, like SurgiWrap™, have high modulus values, making them stiff, and preventing these films from contouring to bodily tissues when implanted. The high modulus values of PLA [see Gruber and O'Brien, 2002, in Biopolymers: Polyesters, III (Doi, Y. and Steinbüchel, A., Eds.) vol. 4, pp. 235-250. Weinheim: Wiley-VCH.] result in films of low toughness, and these properties, combined with other PLA properties, limit the ability of the polymer scientist to process PLA into thin films with good handling properties, for example, by solvent casting and melt extrusion.

U.S. Pat. No. 6,548,569 to Williams et al. discloses an unoriented film of poly-4-hydroxybutyrate produced by compression molding in a batch process, not a continuous process. The film had a tensile strength of 5.27 kgf/mm² (7,500 psi), tensile modulus of 6.6 kgf/mm² (9,400 psi), and elongation at break of 1,000%.

It is an object of the present invention to provide methods to produce films of absorbable polymers that have relatively low modulus values, and which are tough and have high strength.

It is a further object of the present invention to provide continuous processes to produce such films, such as melt processing and solvent casting, as compared to batch processes such as compression molding.

It is another object of the present invention to provide films which can be used in medical applications, for example, as implants such as devices for anti-adhesion barriers, tissue separation and temporary tissue support, coatings on medical devices, including stent coatings, as well as devices for tissue in-growth particularly where the film has been rendered porous.

It is therefore an object of the invention to provide continuous processes for polymer film production which yield materials with excellent physical and mechanical properties, and the resulting polymer films.

SUMMARY OF THE INVENTION

Continuous processing methods for making absorbable polymeric films with one or more of the following properties: high toughness, low modulus, high tensile strength, and thickness less than 10 mm, more preferably less than 1 mm, and more preferably less than 100 μm, have been developed. In the preferred embodiment, the polymer is a polyhydroxyalkanoate, and in the most preferred embodiment, the polymer comprises 4-hydroxybutyrate. A particularly preferred embodiment is a film of poly-4-hydroxybutyrate or copolymer thereof, wherein the film has a tensile strength greater than 5.5 kgf/mm², tensile modulus less than 181 kgf/mm², and elongation at break from 10-500%, wherein the film is derived by a continuous process such as melt extrusion or solvent casting, followed by orientation to more than 25% of the film's original length in one or more directions.

These can be used for a variety of purposes including fabrication of medical devices.

DETAILED DESCRIPTION OF THE INVENTION

Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Cambridge, Mass.).

"Copolymers of poly-4-hydroxybutyrate" as generally used herein means any polymer comprising 4-hydroxybutyrate with one or more different hydroxy acid units.

"Blend" as generally used herein means a physical combination of different polymers, as opposed to a copolymer comprised of two or more different monomers.

Orientation is the process by which the film is stretched beyond its yield point and plastically deformed, but does not break (i.e. it retains mechanical and physical integrity). The degree of orientation may be expressed as the percentage or ratio that the film is stretch when compared to the original film prior to orientation. Films are preferably oriented by stretching the film by at least 25% of the film's original length in one or more directions.

"Tensile modulus" is the ratio of stress to strain for a given material within its proportional limit. As used herein, low tensile modulus means a material having a tensile modulus less than 180 kgf/mm².

"Tensile strength" is the maximum or ultimate tensile load per unit area of original cross section area of the test specimen, within the gauge boundaries, sustained by the specimen during the test. As used herein, high tensile strength means a material test sample having a tensile strength of at least 5.3 kgf/mm².

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993.) As used herein, high toughness means a value greater than 10 kgf/mm².

"Elongation" or extensibility of a material means the amount of increase in length resulting from, as an example, the tension to break a specimen. It is expressed usually as a percentage of the original length. (Rosato's Plastics Encyclopedia and Dictionary, Oxford Univ. Press, 1993.)

"Molecular weight" as used herein, unless otherwise specified, refers to the weight average molecular weight (Mw), not number average molecular weight (Mn).

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

I. Composition

Methods have been developed to produce films of P4HB and copolymers with exceptional toughness. These methods may be used to prepare films that have substantially uniform physical properties and physical integrity. The methods may be run continuously, which is particularly advantageous in manufacturing. These films can be prepared by solution casting or by melt extrusion followed by orientation.

A. Polymers

The processes described herein can typically be used with any of the polyhydroxyalkanoate polymers, including blends and copolymers thereof.

In a preferred embodiment, the polymer is poly-4-hydroxybutyrate (P4HB) or a copolymer thereof. Copolymers include P4HB with 3-hydroxybutyrate, and P4HB with glycolic acid monomer. P4HB and copolymers thereof can be obtained from Tepha, Inc. of Cambridge, Mass.

B. Films

In a preferred embodiment, films can be prepared with thickness of less than 10 mm, more preferably less than 1 mm, and even more preferably less than 100 μm. It has been discovered that very thin films of P4HB polymer or copolymers thereof can be prepared with substantially uniform physical properties, and physical integrity, by solution casting. Using this method, films cast from solutions of the polymer or copolymers dissolved in organic solvents can have thicknesses that are less than 100 μm, and even less than 50 μm. For example, solution cast films of P4HB have been prepared with thicknesses of 20 to 50 μm. With appropriate choice of solvent, polymer and casting conditions, thinner films of P4HB can be produced, or the cast films can be stretched and oriented uniaxially or biaxially to yield thinner and stronger films than the unoriented cast films.

It has also been discovered that very thin films of P4HB and copolymer thereof can be prepared with exceptional toughness and strength. These cast films have a tensile strength of approximately 7.2 kgf/mm$^2$ and elongation to break of approximately 200%. In comparison, a commercially available implantable film of PLA (SurgiWrap™ Bioresorbable Film) has a tensile strength of approximately 5.9 kgf/mm$^2$ and an elongation to break of 95%.

Films of P4HB polymer or copolymers thereof, with exceptional toughness, can be prepared by melt processing followed by orientation (stretching). For example, a film of P4HB may be prepared by melt extrusion followed by stretching. Stretching substantially increases stress as measured in kgf/mm$^2$. For example, the stress in an unoriented P4HB film prepared by melt extrusion, thickness of 0.022 mm and width of 13 mm was measured on a MTS mechanical analyzer to be 4.98 kgf/mm$^2$. The stress in the same P4HB film after stretching the sample 3.6× the original length to a thickness of 0.010 mm and width of 8 mm was measured to be 14.13 kgf/mm$^2$ with an elongation to break of the oriented (or stretched) sample of approximately 25%.

Comparative ball burst testing can be done by ASTM D6797-02, [Standard Test Method for Bursting Strength of Fabrics Constant-Rate-of-Extension (CRE) Ball Burst Test (1 cm ball, 1.6 cm opening)]. This testing shows that P4HB films are stronger and tougher than SurgiWrap™ film, another commercially available, absorbable film used as an implant material. Ball burst strength and elongation for a 40 μm P4HB film were 5.6 kgf and 39 mm (ball displacement at break), respectively, while for SurgiWrap they were 3.2 kgf and 3.4 mm (ball displacement at break), respectively, for a slightly thicker film (50 μm). The higher breaking force and longer extension to break for the P4HB film demonstrate its greater strength and toughness.

In a preferred embodiment, the films described herein have toughness greater than 10 kgf/mm$^2$, more preferably greater than 50 kgf/mm$^2$, and even more preferably greater than 100 kgf/mm$^2$.

In a preferred embodiment, the films described herein preferably have tensile strength greater than 5.5 kgf/mm$^2$, more preferably greater than 7.0 kgf/mm$^2$, and even more preferably greater than 10.0 kgf/mm$^2$.

In a preferred embodiment, the films described herein preferably have an elongation to break greater than 10%, more preferably greater than 15%, and even more preferably greater than 20%.

C. Other Components

The P4HB polymer and copolymer films may contain other materials, including plasticizers, nucleants, other polymers, additives, and compatibilizers. Examples of plasticizers are disclosed by U.S. Pat. No. 6,905,987 to Noda et al. Other components may be added to impart benefits such as, but not limited to, increased stability, including oxidative stability, brightness, color, flexibility, resiliency, workability, processibility (by addition of processing aids), viscosity modifiers, and odor control.

Active components, including therapeutic, diagnostic and/or prophylactic agents, such as drugs, or other substances may be incorporated. Such compositions may be used for controlled release of the drugs or other substances. These may be proteins, peptides, sugars, polysaccharides, glycoproteins, lipids, lipoproteins, nucleic acid molecules, or combinations thereof. Moreover, the films may comprise proteins, polysaccharides, peptides, as well as other substances including allograft and xenograft materials. It may be advantageous to incorporate contrast agents, radiopaque markers, or radioactive substances.

For certain applications it may also be desirable to incorporate fillers, including materials such as titanium dioxide, calcium carbonate, hydroxyapatite, and tricalcium phosphate. Such fillers may include agents that can subsequently be leached or washed out of the film to render it porous.

D. Formation Into Devices

Films made from P4HB polymers and copolymers thereof by solvent casting and melt extrusion are characterized by their thinness, which may be less than 100 μm, and even less than 50 μm. These films are also characterized by high tensile strength and toughness and high ductility prior to orientation. These films have properties that are substantially improved for medical application relative to PLA-based films.

The films possess properties that are desirable in preparing medical products, particularly implantable medical devices. For example, the films may be used to make partially or fully absorbable biocompatible medical devices, or components thereof. Such devices include, but are not limited to: stent, stent graft, stent coating, drug delivery device, device for temporary wound or tissue support, repair patch, tissue engineering scaffold, retention membrane (for example, to retain bone graft), anti-adhesion membrane, tissue separation membrane, hernia repair device, device coating (including devices to improve fixation), cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, including but not limited to atrial septal defect repair devices and PFO closure devices, left atrial appendage (LAA) closure device, pericardial patch, bulking and filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

II. Methods of Manufacturing Films

A. Method of Making P4HB Polymer or Copolymer Films by Solvent Casting

In a preferred method, a film of P4HB polymer or copolymer thereof may be prepared by solution casting as follows. A homogeneous solution of P4HB in a suitable solvent such as 1,4-dioxane or tetrahydrofuran (THF) is prepared at approximately 10-15 wt/vol %. The solution should have a viscosity of approximately 400 to 7,400 cP. The polymer solution is pumped at approximately room temperature through a 150 mm slot die with a 400 μm die gap onto a moving web, for example, of aluminum foil. The web speed is approximately 0.5 m/min and traveled 5 m before being collected on a collection roller. The speed is adjusted to ensure evaporation of the solvent. One or more separate air drying zones set at 50-60° C. were employed to remove solvent from the polymer film before collection on the final roll. A number of parameters can be varied to control the film thickness including, but not limited to, the pump speed, the die gap and width, the polymer concentration and the web speed.

B. Method of Making P4HB Polymer or Copolymer Films by Melt Processing Through Melt Extrusion Films can also be prepared by melt-extrusion methods. Preferred methods are a T-die extrusion method or an inflation method.

In the formation of the film by melt-extrusion, the barrel and T-die temperatures for preferably carrying out the formation are 80 to 250° C., more preferably 100 to 210° C. The melting of the P4HB is insufficient at temperature less than 100° C. When the temperature is higher than 250° C., the P4HB markedly undergoes thermal decomposition. However, the site of the barrel directly below a hopper may have a temperature of less than 100° C. The molten film exits the T-die and is cast over a chilled moving surface preferably, one or more rotating cylindrical cast rollers with surface temperature maintained at 5-100° C., but more preferably at 10° C. This step is followed by a take-up step to wind up the extruded film. Film thickness can be varied by changing the gap of the T-die slit, polymer flow rate, and cast roll speed.

In the formation of film by the inflation method, an inflation molding circular die is used instead of a T-die to extrude cylindrical film of P4HB. The molten cylindrical film is cooled and solidified by blowing it up with cold air blown from the central portion of the circular die, and the cylindrical film which had been blown up is collected with a take-up machine. Film thickness can be varied by changing the gap of the inflation die slit, polymer flow rate, cooling air pressure and temperature and take-up speed.

C. Orientation of Films

The melt-extrusion films and solvent cast films show improved mechanical properties when stretched. The melt-extrusion film may be stretched by several methods such as a roll stretching and/or a stretching method using a tenter frame. The melt-extrusion film can be stretched at a temperature between room temperature and 150° C. at a stretch ratio of 0.25 to 15. To increase the processing rate, the stretching may be more preferably carried out at a temperature in the range of from 40 to 80° C. The stretching may be monoaxial stretching for forming a monoaxially oriented film, consecutive biaxial stretching for forming a biaxially oriented film and simultaneous biaxial stretching for forming a plane-oriented film. When the melt-extrusion film is stretched, the tensile strength at break in the direction in which the film is stretched is increased.

The present invention will be further understood by referenced to the following non-limiting examples.

Example 1

Preparation of Solvent Cast P4HB Film by a Continuous Process

A homogeneous solution of P4HB in 1,4-dioxane (15% wt/vol) was prepared by dissolving 91 g of P4HB in 610 ml of 1,4-dioxane. This solution had a viscosity of approximately 7,400 cP. The polymer solution was pumped at approximately 36 ml/min at room temperature through a 150 mm slot die with a 400 μm die gap onto a moving web of aluminum foil. The web speed was approximately 0.5 m/min and traveled 5 m before being collected on a collection roller. Three separate air drying zones set at 50-60° C. were employed to desolventize the polymer film before collection on the final roll. Using these conditions, a 43 μm thick film was obtained. A thinner film (24 μm thick) was obtained by increasing the web speed to 0.75 m/min and reducing the polymer concentration to 10%. Thinner films may also be obtained by reducing the die gap or pump speed. Mechanical properties of the solvent cast films compared to commercially available SurgiWrap™ 70:30 Poly (L-lactide-co-D,L-lactide) are shown in Tables 1 and 2.

TABLE 1

Tensile mechanical properties of solvent cast P4HB films versus SurgiWrap ™ Bioresorbable Film.

| Description | Thickness (mm) | Tensile Strength (kgf/mm$^2$) | Elongation at break (%) | Tensile Modulus (kgf/mm$^2$) |
|---|---|---|---|---|
| P4HB Solvent Cast Film | 0.043 | 7.2 | 238 | 93 |
| P4HB Solvent Cast Film | 0.024 | 5.6 | 186 | 102 |
| SurgiWrap ™ 70:30 Poly (L-lactide-co-D,L-lactide) | 0.050 | 5.0 | 95 | 181 |

TABLE 2

Ball burst properties of solvent cast P4HB film and SurgiWrap ™ Bioresorbable Film. (1.0 cm ball, 1.6 cm opening, 300 mm/min ball speed per ASTM D6797-2)

| Description | Thickness (mm) | Peak Load (kg) | Ball displacement at break (mm) |
|---|---|---|---|
| P4HB Solvent Cast Film | 0.040 | 5.6 | 39 |
| P4HB Solvent Cast Film | 0.024 | 4.3 | 43 |
| SurgiWrap ™ | 0.050 | 3.2 | 3.4 |

Example 2

Preparation of a P4HB Film by Extrusion Casting and Stretching

P4HB (Tepha, Inc., Cambridge, Mass.) (Mw 506,000) was ground into small pieces using a Fritsch cutting mill (Pulversette 15, 10 mm bottom sieve) and dried under vacuum overnight to less than 0.01% (w/w) water. Dried pellets of the polymer were fed into an extruder barrel of a Leistritz 27 mm, 40:1 L/D co-rotating twin screw extruder fitted with 10 inch wide coat-hanger die with adjustable die lips initially set at 0.015 inch gap. Eleven heating zones of the extruder were set at 75, 90, 110, 110, 130, 130, 130, 150, 150, 200 and 200° C. and the die temperature was set at 200° C. Polymer feed rate was set at 1 lb/hr and the extruder speed was set at 100 rpm. Melt pressure measured 247 psi and melt temperature measured 208° C. A 7-inch diameter roll was used for casting. Roll surface temperature was kept at 12° C. and film line speed was maintained at 3 feet per minute. The properties of a film derived by this process before and after biaxial orientation is shown in Table 3.

TABLE 3

Tensile mechanical properties of P4HB film produced by a melt extrusion process before and after orientation

| Specimen | Thickness (mm) | Width (mm) | Load (kgf) | Tensile Stress (kgf/mm$^2$) | Elongation at Break (%) | Tensile Modulus (kgf/mm$^2$) | Toughness (kgf/mm$^2$) |
|---|---|---|---|---|---|---|---|
| Unoriented | 0.035 | 8 | 1.00 | 5.72 | 515 | 27.8 | 1511 |
| Unoriented | 0.061 | 8 | 1.56 | 5.10 | 561 | 31.8 | 1488 |
| Unoriented | 0.230 | 8 | 6.35 | 5.63 | 1191 | 23.4 | 3747 |
| Biaxially Oriented | 0.010 | 8 | 1.13 | 14.13 | 25.0 | 22.5 | 184 |

Example 3

Comparative Data for Commercial Films

Tables 4 and Table 5 below illustrate the advantageous mechanical properties of P4HB films prepared by the methods described herein. Their tensile properties are compared with films made from an absorbable polymer, L-PLA (L-polylactic acid), unoriented P4HB films produced in this work and with unoriented P4HB films produced in a batch process.

TABLE 4

Tensile Property Comparison

| Samples | Tensile Strength kgf/mm$^2$ | Elongation at Break % | Tensile Modulus kgf/mm$^2$ | Toughness kgf/mm$^2$ |
|---|---|---|---|---|
| P4HB Unoriented Film, Batch Process See U.S. Pat. No. 6,548,569 | 5.27 | 1,000 | 66.0 | N/A |
| P4HB Melt Extruded Unoriented (Average values from Table 3) | 5.48 | 500-1200 | 27.7 | 2249 |
| P4HB Biaxially oriented | 14.13 | 25.0 | 22.5 | 184.0 |
| PLLA Film | 6.32 | 1.50 | 745.6 | 3.875 |

TABLE 5

Ball Burst Strength Comparison (1.0 inch ball, 1.75 inch opening, 300 mm/min ball speed per ASTM D6797-2)

| Samples | Thickness mm | Burst Load kgf | Burst Stress kgf/mm$^2$ | Ball displacement at break mm |
|---|---|---|---|---|
| P4HB Melt Extruded Unoriented | 0.036 | 16.14 | 14.28 | 95.3 |
| P4HB Melt Extruded Unoriented | 0.059 | 19.13 | 11.71 | 87.6 |
| P4HB Melt Extruded Unoriented | 0.226 | 70.42 | 9.92 | 83.0 |
| P4HB Biaxially Oriented | 0.01 | 3.6 | 7.22 | 22.7 |
| PLLA film | 0.100 | 4.5 | 1.88 | 3.3 |
| SurgiWrap | 0.046 | 5.38 | 3.72 | 5.7 |

We claim:

1. A film of poly-4-hydroxybutyrate or copolymer thereof, wherein the film has a tensile strength greater than 5.5 kgf/mm$^2$ and elongation at break from 10-500%, wherein the film is derived by continuous processing of the polymer or copolymer to form a film, followed by orientation such that the film is stretched by more than 25% of the film's original length in one or more directions.

2. The film of claim 1 formed by melt extrusion or solvent casting.

3. The film of claim 1, wherein the film has a tensile strength greater than 10.0 kgf/mm$^2$.

4. The film of claim 1 formed into a device.

5. The film of claim 4 wherein the film is a component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

6. The film of claim 1, wherein the thickness of the film is less than 10.0 mm.

7. The film of claim 1 further comprising a prophylactic, diagnostic, or therapeutic agents.

8. The film of claim 1 further comprising at least one additive selected from the group consisting of other polymers, plasticizers, nucleants, compatibilizers, porogens, radiolabelled substances, imaging agents, radiopaque markers, contrast agents, anti-oxidants, dyes, viscosity modifiers, and odor control agents.

9. A method of producing a film of poly-4-hydroxybutyrate or copolymer thereof, wherein the film has a tensile strength greater than 5.5 kgf/mm$^2$ and wherein the film is derived by a continuous process of solvent casting or melt extrusion of the polymer to form a film, followed by orientation of the film such that the film is stretched by more than 25% of the film's original length in one or more directions.

10. The method of claim 9 further comprising forming the film into a component of a device selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

11. A method of using a device comprising a film of poly-4-hydroxybutyrate or copolymer thereof, wherein the film has a tensile strength greater than 5.5 kgf/mm² and wherein the film is derived by a continuous process of solvent casting or melt extrusion of the polymer to form a film, followed by orientation of the film such that the film is stretched by more than 25% of the film's original length in one or more directions, comprising inserting or implanting the device into an individual in need thereof.

12. The method of claim 11 wherein the device is selected from the group consisting of a stent, stent graft, stent coating, drug delivery device, device for temporary wound or tissue support, repair patch, tissue engineering scaffold, retention membrane, anti-adhesion membrane, tissue separation membrane, hernia repair device, device coating, cardiovascular patch, catheter balloon, vascular closure device, sling, biocompatible coating, rotator cuff repair device, meniscus repair device, adhesion barrier, guided tissue repair/regeneration device, articular cartilage repair device, nerve guide, tendon repair device, intracardiac septal defect repair device, atrial septal defect repair devices, patent foramen ovale (PFO) closure devices, left atrial appendage (LAA) closure device, pericardial patch, bulking agent, filling agent, vein valve, heart valve, bone marrow scaffold, meniscus regeneration device, ligament and tendon graft, ocular cell implant, spinal fusion device, imaging device, skin substitute, dural substitute, bone graft substitute, wound dressing, and hemostat.

13. The film of claim 1, wherein the thickness of the film is less than 1.0 mm.

14. The film of claim 1, wherein the thickness of the film is less than 100 μm.

15. The film of claim 1 having a toughness greater than 10.0 kgf/mm².

16. The film of claim 1 having a toughness of about 184 kgf/mm² and a tensile strength of about 14.13 kgf/mm².

* * * * *